US012635888B2

(12) United States Patent
Zakaria et al.

(10) Patent No.: US 12,635,888 B2
(45) Date of Patent: May 26, 2026

(54) DUAL FREQUENCY COMB PORTABLE PHOTOACOUSTIC IMAGING DEVICE FOR NON-INVASIVE MEDICAL IMAGING AND ASSOCIATED METHODS

(71) Applicant: Honeywell International Inc., Charlotte, NC (US)

(72) Inventors: Ryadh Zakaria, Waterlooville HANTS (GB); Chad Hoyt, Roseville, MN (US); Manan Atit, Irving, TX (US); Moin Shafai, Plano, TX (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 18/440,759

(22) Filed: Feb. 13, 2024

(65) Prior Publication Data

US 2025/0255489 A1 Aug. 14, 2025

(51) Int. Cl.
*A61B 5/00* (2006.01)

(52) U.S. Cl.
CPC .......... *A61B 5/0095* (2013.01); *A61B 5/6805* (2013.01); *A61B 2560/0431* (2013.01)

(58) Field of Classification Search
CPC ............................. A61B 5/0095; A61B 5/6805
See application file for complete search history.

(56) References Cited

U.S. PATENT DOCUMENTS

| | | | |
|---|---|---|---|
| 5,769,076 | A | 6/1998 | Maekawa et al. |
| 10,101,268 | B2 | 10/2018 | Apolonskiy et al. |
| 11,429,010 | B1 | 8/2022 | Puckett et al. |

(Continued)

FOREIGN PATENT DOCUMENTS

| | | |
|---|---|---|
| CN | 113552071 A | 10/2021 |
| JP | 2019-207684 A | 12/2019 |

(Continued)

OTHER PUBLICATIONS

Liu et al., Photoacoustic imaging of the eye: A mini review, Photoacoustics, vol. 4, Issue 3, Sep. 2016, pp. 112-123. https://doi.org/10.1016/j.pacs.2016.05.001 (Year: 2016).*

(Continued)

*Primary Examiner* — John D Li
(74) *Attorney, Agent, or Firm* — Alston & Bird LLP

(57) ABSTRACT

In accordance with various embodiments of the present disclosure, a device for non-invasive medical imaging is provided. In some embodiments, the device comprises a photonic integrated circuit scale dual frequency comb (DFC), a hand-held wand, and at least one processing element. The wand comprises at least one emission point for emitting light from the DFC at a plurality of different wavelengths and at least three sensors. The wand directs the emitted light at one or more bodily structures. The sensors are adapted to detect acoustic waves from thermo-elastic changes in one or more elements within the bodily structures. The processing element is for generating an optical absorption spectrum from the detected acoustic waves, identifying one or more elements within the bodily structures based on the optical absorption spectrum, and generating a three-dimensional image of the elements based on the optical absorption spectrum from the detected acoustic waves.

20 Claims, 6 Drawing Sheets

(56) References Cited

U.S. PATENT DOCUMENTS

| | | | | |
|---|---|---|---|---|
| 11,754,824 | B2 | 9/2023 | Ince et al. | |
| 11,906,875 | B2 | 2/2024 | Puckett et al. | |
| 12,019,353 | B2 | 6/2024 | Puckett et al. | |
| 12,169,349 | B2 | 12/2024 | Puckett et al. | |
| 12,218,483 | B2 | 2/2025 | Puckett et al. | |
| 2006/0100489 | A1* | 5/2006 | Pesach | A61B 5/0084 |
| | | | | 600/310 |
| 2008/0021331 | A1 | 1/2008 | Grinvald et al. | |
| 2009/0287076 | A1 | 11/2009 | Boyden et al. | |
| 2010/0245770 | A1 | 9/2010 | Zhang et al. | |
| 2013/0289381 | A1 | 10/2013 | Oraevsky et al. | |
| 2014/0316239 | A1* | 10/2014 | Kasamatsu | H01S 3/0912 |
| | | | | 600/407 |
| 2018/0035891 | A1 | 2/2018 | Van Soest et al. | |
| 2019/0003958 | A1* | 1/2019 | Nanaumi | G01N 21/1702 |
| 2019/0099083 | A1* | 4/2019 | Fukui | G06T 7/11 |
| 2019/0307405 | A1 | 10/2019 | Terry et al. | |
| 2022/0133273 | A1 | 5/2022 | Dangi et al. | |
| 2023/0184657 | A1 | 6/2023 | Brown et al. | |
| 2023/0208101 | A1* | 6/2023 | Kuyken | H01S 5/1025 |
| | | | | 356/326 |
| 2023/0248244 | A1* | 8/2023 | Holzwarth | A61B 5/0035 |
| | | | | 600/407 |
| 2024/0110858 | A1 | 4/2024 | Kishore et al. | |
| 2024/0130709 | A1* | 4/2024 | Prough, III | A61B 5/14542 |
| 2024/0332896 | A1 | 10/2024 | Lenin et al. | |

FOREIGN PATENT DOCUMENTS

| | | | |
|---|---|---|---|
| WO | 2022/011133 | A1 | 1/2022 |
| WO | 2022/131612 | A1 | 6/2022 |
| WO | 2023/132792 | A2 | 7/2023 |

OTHER PUBLICATIONS

Biswas, Deblina, et al., "Investigation of diseases through red blood cells' shape using photoacoustic response technique", Proceedings of SPIE—Dynamics and Fluctuations in Biomedical Photonics XII, Mar. 5, 2015, pp. 93220K-1 thru 93220K-5, vol. 9322, Society of Photographic Instrumentation Engineers, US.

Extended European Search Report Mailed on Mar. 21, 2025 for EP Application No. 25154216, 12 page(s).

Extended European Search Report Mailed on Mar. 26, 2025 for EP Application No. 25154218, 11 page(s).

Extended European Search Report Mailed on Mar. 26, 2025 for EP Application No. 25154389, 10 page(s).

Hilde Jans et al., "The sound of light: photoacoustics for biomedical applications," Spectroscopy Europe, 34(1):22-26, (2022).

Imec International, "The sound of light: photoacoustics for biomedical applications", retrieved from the Internet at URL: <https://www.imec-int.com/en/articles/sound-light-photoacoustics-biomedical-applications> on Oct. 18, 2024, 8 pages.

Jacob T. Friedlein et al., "Dual-comb photoacoustic spectroscopy," Nature Communications, 11:1-10, (Jun. 19, 2020).

Kenichi Nagae et al., "Real-time 3D Photoacoustic Visualization System with a Wide Field of View for Imaging Human Limbs [version 2; referees: 2 approved]," F1000Research, 7(1813):1-25, (Feb. 28, 2019). [Retrieved from the Internet Oct. 18, 2024: URL: <https://www.ncbi.nlm.nih.gov/pmc/articles/PMC6396844/>].

Miller, Steven A., et al., "Tunable Frequency Combs Based on Dual Microring Resonators," Optics Express, published Aug. 7, 2015, pp. 21527-21540, vol. 23, No. 16, retrieved from the Internet at https://opg.optica.org/directpdfaccess/ef728c4b-2ba3-4682-a8f70177d3bf53f1_323870/oe-23-16-21527.pdf?da=1&id=323870&seq=0&mobile=no on Jan. 31, 2025.

Non-Final Rejection Mailed on Apr. 24, 2025 for U.S. Appl. No. 18/440,786, 36 page(s).

Roy G.M. Kolkman et al., "Photoacoustic imaging of tumor angiogenesis," Proceedings of SPIE—The International Society for Optical Engineering, 6856:1-6, (Mar. 2008). [Retrieved from the Internet Oct. 5, 2023: URL: <https://www.researchgate.net/publication/252464626_Photoacoustic_imaging_of_tumor_angiogenesis/link/5458927e0cf2bccc491143f0/download>].

Steven A. Miller et al., "Tunable Frequency Combs Based on Dual Microring Resonators," Optics Express, 23(16):21527-21540, (2015). [Retrieved from the Internet Nov. 4, 2024: URL: <https://opg.optica.org/oe/fulltext.cfm?uri=oe-23-16-21527&id=323870].

Thibault Wildi et al., "Photo-acoustic dual-frequency comb spectroscopy," Nature Communications, 11(4164):1-6, (Aug. 20, 2020). [Retrieved from the Internet Oct. 5, 2023: URL: <https://bib-pubdb1.desy.de/record/449179/files/s41467-020-17908-9.pdf?subformat=pdfa&version=1>].

U.S. Non-Provisional Patent Application for "System and Method of Efficient Optical Frequency Comb Generation on Optical Waveguides", Unpublished (Filed May 17, 2024), Chad Hoyt (Inventor), Honeywell International Inc. (Applicant), 18667083.

Wildi, Thibault, et al., "Photo-acoustic dual-frequency comb spectroscopy", Nature Communications, published online Aug. 20, 2020, retrieved from the Internet at https://bib-pubdb1.desy.de/record/449179/files/s41467-020-17908-9.pdf?subformat=pdfa&version=1 on Jan. 31, 2025, 6 pages.

Wonseok Choi et al., "Three-dimensional Multistructural Quantitative Photoacoustic and US Imaging of Human Feet in Vivo," Radiology, 303(2):467-473, (May 2022). [Retrieved from the Internet Oct. 18, 2024: URL: <https://pubs.rsna.org/doi/full/10.1148/radiol.211029>].

* cited by examiner

DUAL FREQUENCY COMB PORTABLE PHOTOACOUSTIC IMAGING DEVICE FOR NON-INVASIVE MEDICAL IMAGING AND ASSOCIATED METHODS

FIELD OF THE INVENTION

Example embodiments of the present disclosure relate generally to medical imaging devices and, more particularly, to photoacoustic medical imaging devices and methods.

BACKGROUND

Traditional modalities of medical imaging (e.g., computed tomography (CT), magnetic resonance imaging (MRI), X-ray, etc.) can be invasive, expensive, and require specialized training to operate (often due to health risks associated with operating such modalities). Further, such traditional medical imaging modalities require devices that are physically large and/or that have very specific siting requirements. As such, these traditional medical imaging modalities are not well suited for point-of-care use (e.g., in a primary care environment). The cost and inconvenience of such traditional medical imaging modalities limit their use for routine screening and may even reduce their suitability for specific diagnostic uses and treatment/procedure follow-up imaging.

Through applied effort, ingenuity, and innovation, many of these identified problems have been solved by developing solutions that are included in embodiments of the present disclosure, many examples of which are described in detail herein.

BRIEF SUMMARY

Various embodiments described herein relate to devices and methods for non-invasive medical imaging.

In accordance with various embodiments of the present disclosure, a device for non-invasive medical imaging is provided. In some embodiments, the device comprises a photonic integrated circuit (PIC)-scale dual frequency comb (DFC), a hand-held wand, and at least one processing element. The hand-held wand comprises (i) at least one emission point for emitting light from the PIC-scale DFC at a plurality of different wavelengths and (ii) at least three sensors. The hand-held wand is adapted to direct the emitted light at one or more bodily structures of an animal. The at least three sensors are adapted to detect acoustic waves from thermo-elastic changes in one or more elements within the one or more bodily structures exposed to the emitted light. The at least one processing element is for (i) generating an optical absorption spectrum from the detected acoustic waves from each of at least three sensors, (ii) identifying at least one of the one or more elements within the one or more bodily structures exposed to the emitted light based on the optical absorption spectrum, and (iii) generating a three-dimensional (3-D) image of the one or more elements based on the optical absorption spectrum from the detected acoustic waves from each of the at least three sensors.

In some embodiments, the PIC-scale DFC resides in the wand.

In some embodiments, the device further comprises a base unit separate from the wand and a display element within the base unit for displaying the generated 3-D image.

In some embodiments, the PIC-scale DFC resides in the base unit.

In some embodiments, the device further comprises one or more optical fiber cables for carrying light from the PIC-scale DFC in the base unit to the at least one emission point in the wand.

In some embodiments, the at least one processing element resides in the wand or the base unit.

In some embodiments, communication between the wand and the base unit is wired or wireless.

In some embodiments, the at least three sensors comprise at least three transducers.

In some embodiments, the at least one processing element provides the generated 3-D image to an artificial intelligence algorithm.

In some embodiments, the one or more elements comprise two elements, the two elements comprise oxygenated blood and non-oxygenated blood, and generating the 3-D image by the at least one processing element comprises generating a 3-D image of one or more blood vessels based on the detected acoustic waves from the oxygenated blood and the non-oxygenated blood.

In some embodiments, the one or more bodily structures comprises an eyeball, relatively shorter wavelengths of light are used to image a posterior portion of the eyeball, and relatively longer wavelengths of light are used to image an anterior portion of the eyeball.

In some embodiments, the one or more bodily structures comprises skin.

In accordance with various embodiments of the present disclosure, a method for non-invasive medical imaging is provided. In some embodiments, the method comprises emitting light from a photonic integrated circuit (PIC)-scale dual frequency comb (DFC) at a plurality of different wavelengths via a hand-held device directed at one or more bodily structures of an animal, detecting acoustic waves from thermo-elastic changes in one or more elements within the one or more bodily structures exposed to the emitted light via one or more sensors in the hand-held device, generating an optical absorption spectrum from the detected acoustic waves, and identifying at least one of the one or more elements within the one or more bodily structures exposed to the emitted light based on the optical absorption spectrum.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1:
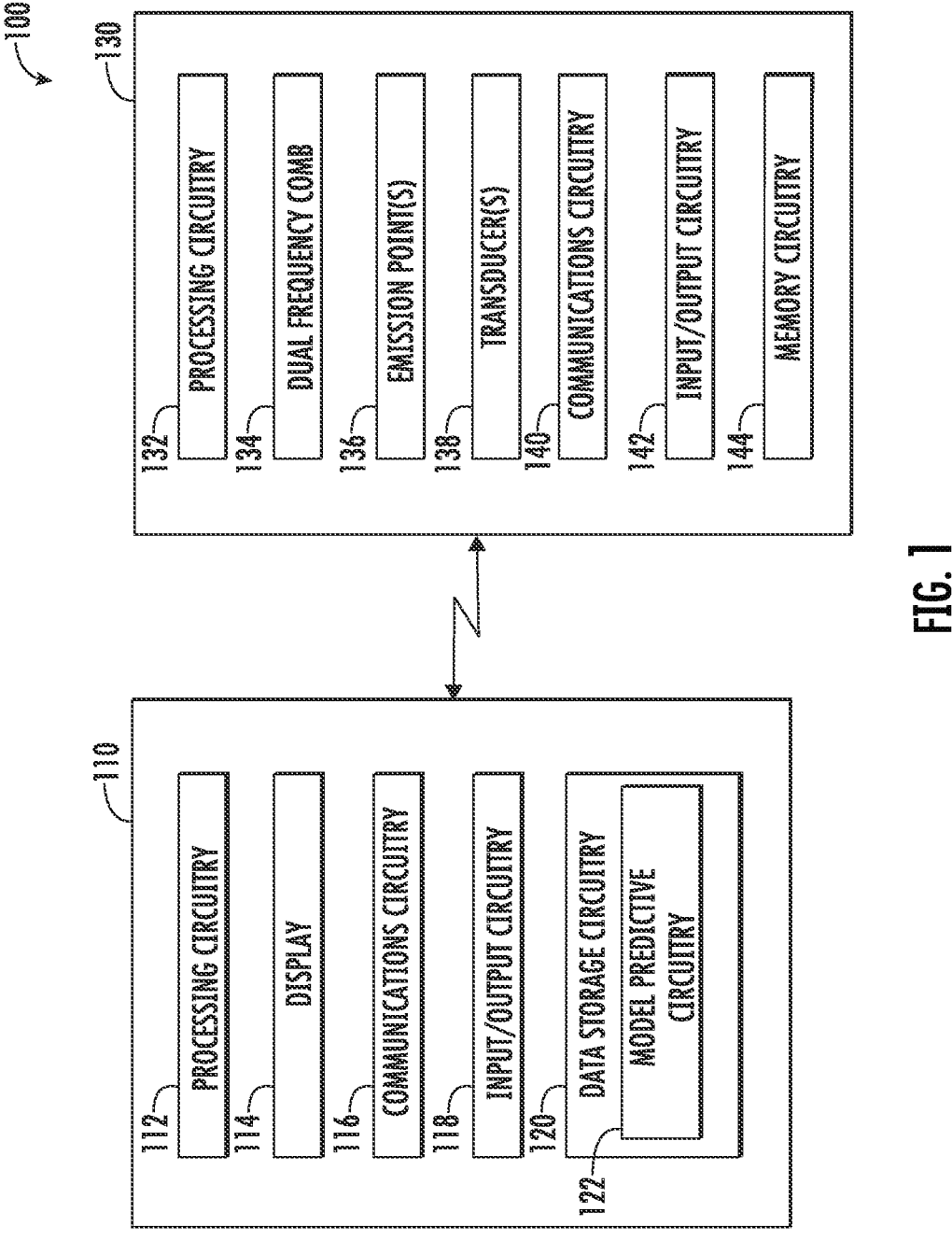
FIG. 1 is an example block diagram of an example device for non-invasive medical imaging in accordance with example embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

As used herein, terms such as "front," "rear," "top," etc. are used for explanatory purposes in the examples provided below to describe the relative position of certain components or portions of components. Furthermore, as would be evident to one of ordinary skill in the art in light of the present disclosure, the terms "substantially" and "approximately" indicate that the referenced element or associated description is accurate to within applicable engineering tolerances.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "according to one embodiment," "in some embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such a component or feature may be optionally included in some embodiments, or it may be excluded.

Various embodiments of the present disclosure provide devices and methods for non-invasive medical imaging. Various embodiments of the present disclosure may be used on any suitable animals, including, but not limited to, humans.

Various embodiments of the present disclosure use a photonic integrated circuit (PIC)-scale dual frequency comb (DFC) laser source to provide a portable, non-radioactive, point-of-care photoacoustic imaging device which can be used for continuous patient monitoring in a primary care setting without having the need to go for a specialized medical imaging care facility. The term "PIC-scale DFC" refers to a DFC that is implemented on a single integrated circuit ("chip"). The use of a PIC-scale DFC enables devices of various embodiments of the present disclosure to be highly miniaturized and extremely portable. For example, devices of various embodiments of the present disclosure may be hand-held and about the size of a smartphone or may include a hand-held scanning portion that is about the size of a smartphone. Various embodiments of the present disclosure use a PIC-scale fiber optic ring resonator. Further details of implementing a frequency comb using a dual microring resonator are found in "Tunable Frequency Combs Based on Dual Microring Resonators," by Miller et al, Optics Express Vol. 23, Issue 16, pp. 21527-21540 (2015), the contents of which are incorporated herein by reference.

In DFC spectroscopy, two stabilized combs are used to map optical absorption in an absorbing sample to radio frequency (RF) signals for straightforward analysis. These two combs have slightly different repetition rates, generating a large series of beat frequencies on a photodetector that are modulated by sample absorption. Combs can be spectrally broad—greater than an octave in some cases—and therefore provide a broad spectral absorption analysis of the sample.

DFC technology can be applied to photoacoustic imaging in the same way as it is applied to gas spectroscopy: sample molecules and structures uniquely absorb the dual comb laser light and undergoes rapid thermo-elastic change, which in turns results in acoustic waves. These acoustic waves can be picked up by ultrasonic transducers. Processing of the photoacoustic signal generates a broad optical absorption spectrum of the sample, from which the types of cell, molecules, or structures of blood vessels can be identified and imaged based on a predetermination of which types of cells, molecules, tissues, structures, etc., absorb light at which frequency.

Various embodiments of the present disclosure provide devices and methods for non-invasive medical imaging that provide multi-spectral medical imaging capability from a single scan and may be used for any suitable medical imaging studies, for imaging any suitable bodily structures, and for any suitable purpose. For example, various embodiments of the present disclosure may be used for vasculature imaging (for example, for cardiac angiography, ophthalmological screening, tumor angiogenesis detection, sickle cell disease detection and monitoring, etc.), endoscopic scans for gastroenterology, non-invasive skin "biopsies" for dermatology, and many other applications.

Various embodiments of the present disclosure use artificial intelligence (AI)-enabled image processing algorithms to reduce the need for extensive training on the part of a human operator. The portable nature of this imaging device and its AI capabilities will provide treatment solutions that can be personalized and offer long term remote patient monitoring capabilities. Various embodiments of the present disclosure are configured to generate a report of the results of the imaging. In various embodiments, such AI-enabled image processing algorithms are trained to recognize normal and abnormal structures, cells, etc. using a large database of training images of normal and abnormal structures, cells, etc.

To train the AI-enabled image processing algorithm to analyze the generated images and determine if the image shows normal or abnormal structures, cells, etc., a sufficiently high number (typically thousands or tens of thousands) of normal and abnormal images are input into a predictive model training or learning system of the AI-enabled image processing algorithm. Various embodiments of the present disclosures may implement artificial intelligence and/or machine learning algorithms for image analysis that include, but are not limited to, Linear Regression algorithm, Logistic Regression algorithm, Decision Tree algorithm, support vector machine (SVM) algorithm, Naive Bayes algorithm, k-nearest neighbors (KNN) algorithm, K-Means algorithm, Random Forest algorithm, recurrent neural network (RNN) algorithm, generative adversarial network (GAN) algorithm, artificial neural network, and/or the like, to generate the predictive model.

By utilizing DFC technology that can penetrate about 10-15 centimeters (cm) into a body, various embodiments of the present disclosure are capable of imaging many different types of bodily structures, tissues, cells, etc. For example, by detecting oxygenated and deoxygenated blood (which react to two different wavelengths of light), various embodiments of the present disclosure can render accurate blood flow and therefore accurate vasculature images.

Various embodiments of the present disclosure use multiple light sources (e.g., multiple DFCs each with a single corresponding emission point and/or one DFC with multiple emission points) and multiple sensors (e.g., transducers) to capture images from multiple angles that are combined digitally to create three-dimensional (3-D) images, such as of the vasculature/blood flow.

Various embodiments of the present disclosure are able to capture each image very quickly (in one example embodiment, in less than about fifteen micro-seconds), thereby enabling high resolution, motion-tolerant imaging.

While various embodiments of the present disclosure are described herein using a PIC-scale DFC, in some alternative embodiments of the present disclosure a DFC that is not PIC-scale may be used.

Ophthalmological Applications

Current methods of eye imaging are expensive, inaccessible, and time-consuming. Traditional eye imaging methods, such as optical coherence tomography (OCT), require specialized equipment and trained technicians which makes them expensive and inaccessible to many patients, especially those in rural or underserved areas. Additionally, OCT scans can take several minutes to complete, which can be a challenge for patients who are uncomfortable or uncooperative.

Various embodiments of the present disclosure address these problems by providing non-invasive, affordable, and real-time point-of-care eye imaging devices and methods using PIC-scale DFC light source based photoacoustic imaging. Such devices and methods can be used by non-specialists and can provide real-time images of the retina and its vasculature, which can be used to diagnose and monitor a variety of eye diseases. Various embodiments of the present disclosure provide a comprehensive means to screen for a variety of treatable/reversible eye diseases.

Various embodiments of the present disclosure are able to tune multiple laser wavelengths at the same time, with shorter wavelengths (e.g., 800 nm) imaging the posterior structures of the eye (e.g., the retina) and the longer wavelengths (e.g., 1000 nm) imaging the anterior structures of the eye (e.g., the cornea and lens). Imaging the posterior structures of the eye enables detection of, for example, macular degeneration or diabetic retinopathy. Imaging the anterior structures of the eye enables detection of, for example, glaucoma.

Cardiological Applications

Current methods of cardiothoracic disease/injury detection and recovery monitoring (e.g., angiography and computed tomography angiography) are limited by their reliance on symptoms, invasive procedures, or expensive and inaccessible imaging. This can lead to late diagnosis of recurrence, which is a significant risk factor for a myocardial infarction (MI) (i.e., "heart attack").

Various embodiments of the present disclosure address these problems by providing non-invasive, affordable, and real-time point-of-care cardiac imaging devices and methods using PIC-scale DFC light source based photoacoustic imaging. Such devices and methods enable frequent/continuous monitoring of patient cardiac recovery (e.g., post-MI or post-surgery (e.g., angioplasty, coronary artery bypass graft, etc.)) in a general cardiologist care setting, in a primary care setting, or even in a pre-hospital emergency medical setting.

Various embodiments of the present disclosure enable detection/monitoring of a variety of cardiac conditions, including, but not limited to, coronary artery disease, aortic aneurysm, peripheral vascular disease, stent health, therapy guidance, post-surgical hemorrhage assessments, and recovery. Various embodiments of the present disclosure enable imaging of a patient's coronary arteries without the use of radioactive contrast dye or radiation, enabling more frequent imaging. Various embodiments of the present disclosure enable radiation-free imaging of a patient undergoing an angioplasty procedure.

Devices of various embodiments of the present disclosure may be worn by a patient (i.e., "body-worn") or may include a scanning portion that is body-worn. Such devices may be worn on any suitable body part of a patient, depending on the structures to be imaged, such as, but not limited to, chest, abdomen, arm, or leg. For example, devices of various embodiments of the present disclosure may be implemented as a vest, harness, or the like that is placed on or around (partially or completely) a patient's thorax to image the patient's coronary arteries or other thoracic structures.

In various embodiments of the present disclosure, such a body-worn device or body-worn scanning portion comprises a plurality of emission points positioned about the body-worn device or scanning portion, such that light from a DFC is emitted at each emission point (typically sequentially) toward the patient's body. In some embodiments, there are multiple DFCs, each providing light to a single corresponding emission point. In some other embodiments, there is one DFC that provides light to multiple emission points via optical fiber cables. In various embodiments of the present disclosure, such a body-worn device or body-worn scanning portion comprises a plurality (e.g., three or more) of sensors (e.g., transducers) adjacent to each emission point. In various embodiments of the present disclosure, the plurality of emission points are positioned about the body-worn device or scanning portion such that various aspects of the patient's body (e.g., anterior, posterior, lateral) can be imaged.

Oncological Applications

Current methods of cancer screening, such as biopsies and endovascular visualization, are invasive and expensive. They also require specialized equipment and trained personnel. Various embodiments of the present disclosure address these problems by providing non-invasive, affordable, and real-time point-of-care cancer screening/imaging devices and methods using PIC-scale DFC light source based photoacoustic imaging. Such devices and methods enable frequent patient screening/monitoring in a medical office setting. For example, various embodiments of the present disclosure enable photoacoustic imaging of blood vessels for early detection of cancer and for continuous remote monitoring of angiogenesis. Tumor angiogenesis is the process by which tumors grow new blood vessels and is essential for tumor growth and metastasis. Various embodiments of the present disclosure enable detection of tumor cells circulating within a patient's blood vessels.

Various embodiments of the present disclosure enable monitoring and measurement of tumor angiogenesis before and after treatment, which can be used to personalize cancer therapy and improve patient outcomes. Various embodiments of the present disclosure may lower the rate of cancer-related death due to metastases, allow more frequent monitoring of angiogenesis and quick interventional therapy development, enable earlier detection and treatment, identify early signs of recurrence, and allow a radiation-free imaging solution, which will be beneficial for such an immunocompromised patient population.

Various embodiments of the present disclosure enable the creation of images of the vascular structures in the area around tumor sites, suspected tumor sites, and/or potential tumor sites. Various embodiments of the present disclosure use an AI algorithm that has been trained to recognize the unique vascular structure indicative of tumor sites.

Referring now to the figures, FIG. 1 is an example block diagram of an example imaging device for non-invasive medical imaging in accordance with example embodiments of the present disclosure. The imaging device 100 of FIG. 1 comprises a base unit 110 and a scanning portion 130. In some embodiments, the scanning portion 130 comprises a hand-held device (described further below in relation to FIG. 5) or a body-worn device (described further below in relation to FIG. 6). In some embodiments, the base unit 110 comprises a mobile (e.g., wheeled) housing. In some embodiments, communication between the base unit 110 and the scanning portion 130 is via a wireless connection (e.g., Bluetooth), while in other embodiments such communication is via a wired connection. While the base unit 110 and the scanning portion 130 are illustrated in FIG. 1 as two separate components, in some embodiments the imaging device may comprise a single component encompassing all of the functionality described herein.

In the illustrated embodiment of FIG. 1, the base unit comprises processing circuitry 112, a display 114, communications circuitry 116, input/output circuitry 118, and data storage circuitry 120. Model predictive circuitry 122 is stored in the data storage circuitry 120. In the illustrated embodiment of FIG. 1, the scanning portion 130 comprises processing circuitry 132, a PIC-scale DFC 134, one or more emission points 136 (typically at least three) from which light from the DFC 134 is emitted at the patient, one or more transducers 138 or other suitable sensors (typically at least three for each emission point) to detect acoustic waves from thermo-elastic changes in one or more elements within one or more bodily structures exposed to the emitted light, communications circuitry 140, input/output circuitry 142, and memory circuitry 144.

In the illustrated embodiment of FIG. 1, the processing circuitry 112 controls the operation of at least the base unit 110, the display 114 displays one or more generated images, the communications circuitry 116 enables communication with the scanning portion 130 and/or one or more external devices, such as central servers and/or the like, the input/output circuitry 118 enables a user to interface with the base unit 110, the data storage circuitry 120 stores instructions executed by the processing circuitry 112, and the model predictive circuitry 122 executes one or more AI-enabled image processing algorithms that have been trained to recognize normal and abnormal structures, cells, etc. in the generated image(s).

Further in the illustrated embodiment of FIG. 1, the processing circuitry 132 controls the operation of at least the scanning portion 130, the DFC 134 produces the multi-spectral light emitted by the emission point(s) 136, the transducer(s) detect acoustic waves from thermo-elastic changes in one or more elements within one or more bodily structures exposed to the emitted light, the communications circuitry 140 enables communication with the base unit 110 and/or one or more external devices, the input/output circuitry 142 enables a user to interface with the scanning portion 130, and the memory circuitry 144 stores instructions executed by the processing circuitry 132.

In the embodiment illustrated in FIG. 1, the DFC resides in the scanning portion (e.g., a hand-held device or a body-worn device) which enables a wireless connection between the base unit and the scanning portion since light does not need to be transmitted between the base unit and the scanning portion (although a wired connection may still be desired to ensure robust communications between the scanning portion and the base unit). In the embodiment illustrated in FIG. 2, the DFC resides in the base unit which requires at least a physical connection between the base unit and the scanning portion for transmission of light between the DFC in the base unit and the scanning portion (e.g., an optical fiber cable).

Figure 2:
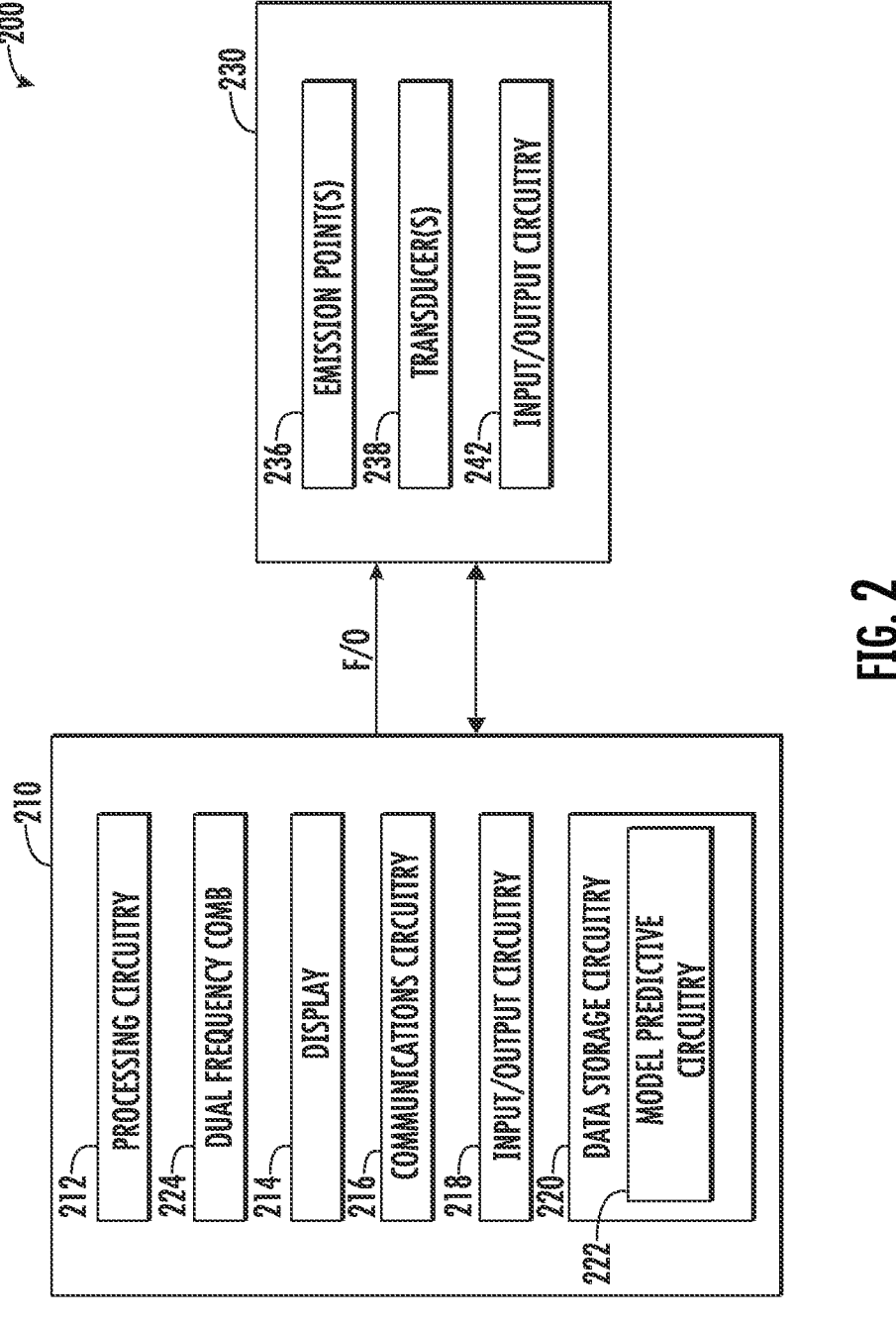
FIG. 2 is an example block diagram of an example device for non-invasive medical imaging in accordance with alternative example embodiments of the present disclosure.

Referring now to FIG. 2, an example block diagram is illustrated of an example imaging device for non-invasive medical imaging in accordance with alternative example embodiments of the present disclosure. The imaging device 200 of FIG. 2 comprises a base unit 210 and a scanning portion 230. In some embodiments, the scanning portion 230 comprises a hand-held device (described further below in relation to FIG. 5) or a body-worn device (described further below in relation to FIG. 6). In some embodiments, the base unit 210 comprises a mobile (e.g., wheeled) housing. In some embodiments, communication between the base unit 210 and the scanning portion 230 is via a wired connection. While the base unit 210 and the scanning portion 230 are illustrated in FIG. 2 as two separate components, in some embodiments the imaging device may comprise a single component encompassing all of the functionality described herein.

In the illustrated embodiment of FIG. 2, the base unit comprises processing circuitry 212, a PIC-scale DFC 224, a display 214, communications circuitry 216, input/output circuitry 218, and data storage circuitry 220. Model predictive circuitry 222 is stored in the data storage circuitry 220. In the illustrated embodiment of FIG. 2, the scanning portion 230 comprises one or more emission points 236 (typically at least three) from which light from the DFC 224 is emitted at the patient, one or more transducers 238 or other suitable sensors (typically at least three for each emission point) to detect acoustic waves from thermo-elastic changes in one or more elements within one or more bodily structures exposed to the emitted light, and input/output circuitry 242.

In the illustrated embodiment of FIG. 2, the processing circuitry 212 controls the operation of at least the base unit 210, the DFC 224 produces the multi-spectral light emitted by the emission point(s) 236, the display 214 displays one or more generated images, the communications circuitry 216 enables communication with the scanning portion 230 and/ or one or more external devices, such as central servers and/or the like, the input/output circuitry 218 enables a user to interface with the base unit 210, the data storage circuitry 220 stores instructions executed by the processing circuitry 212, and the model predictive circuitry 222 executes one or more AI-enabled image processing algorithms that have been trained to recognize normal and abnormal structures, cells, etc. in the generated image(s).

Further in the illustrated embodiment of FIG. 2, the emission point(s) 236 emit the multi-spectral light from the DFC 224, the transducer(s) detect acoustic waves from thermo-elastic changes in one or more elements within one or more bodily structures exposed to the emitted light, and the input/output circuitry 242 enables a user to interface with the scanning portion 230.

The device 100, 200 may be configured to execute the operations described herein. Although the components are described with respect to functional limitations, it should be understood that the particular implementations necessarily include the use of particular hardware. It should also be understood that certain of the components described herein may include similar or common hardware. For example, two sets of circuitries may both leverage use of the same processor, network interface, storage medium, or the like to perform their associated functions, such that duplicate hardware is not required for each set of circuitries.

The use of the term "circuitry" as used herein with respect to components of the device should therefore be understood to include particular hardware configured to perform the functions associated with the particular circuitry as described herein. The term "circuitry" should be understood broadly to include hardware and, in some embodiments, software for configuring the hardware. For example, in some embodiments, "circuitry" may include processing circuitry, storage media, network interfaces, input/output devices, and/or the like. In some embodiments, other elements of the device 100, 200 may provide or supplement the functionality of particular circuitry. For example, the processing circuitry 112, 132, 212 may provide processing functionality, the communications circuitry 116, 140, 216 may provide network interface functionality, the data storage circuitry 120, 220 and/or the memory circuitry 144 may provide storage functionality, and/or the like.

In some embodiments, the processing circuitry 112, 132, 212 (and/or co-processor or any other processing circuitry assisting or otherwise associated with the processor) may be in communication with the data storage circuitry 120, 220 and/or the memory circuitry 144 via a bus for passing information among components of the device. The processing circuitry 112, 132, 212 may be embodied in a number of different ways and may, for example, include one or more processing devices configured to perform independently. Additionally, or alternatively, the processing circuitry 112, 132, 212 may include one or more processors configured in tandem via a bus to enable independent execution of instructions, pipelining, and/or multithreading. The use of the term "processing circuitry" may be understood to include a single core processor, a multi-core processor, multiple processors internal to the device, and/or remote or "cloud" processors.

For example, the processing circuitry 112, 132, 212 may be embodied as one or more complex programmable logic devices (CPLDs), microprocessors, multi-core processors, co-processing entities, application-specific instruction-set processors (ASIPs), and/or controllers. Further, the processing circuitry 112, 132, 212 may be embodied as one or more other processing devices or circuitry. The term circuitry may refer to an entirely hardware embodiment or a combination of hardware and computer program products. Thus, the processing circuitry 112, 132, 212 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing circuitry 112, 132, 212 may be configured for a particular use or configured to execute instructions stored in volatile or non-volatile media or otherwise accessible to the processing circuitry 112, 132, 212. As such, whether configured by hardware or computer program products, or by a combination thereof, the processing circuitry 112, 132, 212 may be capable of performing steps or operations according to embodiments of the present disclosure when configured accordingly.

In an example embodiment, the processing circuitry 112, 132, 212 may be configured to execute instructions stored in the data storage circuitry 120, 220 and/or the memory circuitry 144 or otherwise accessible to the processor. Alternatively, or additionally, the processing circuitry 112, 132, 212 may be configured to execute hard-coded functionality. As such, whether configured by hardware or software methods, or by a combination thereof, the processor may represent an entity (e.g., physically embodied in circuitry) capable of performing operations according to an embodiment of the present disclosure while configured accordingly. Alternatively, as another example, when the processing circuitry 112, 132, 212 is embodied as an executor of software instructions, the instructions may specifically configure the processor to perform the algorithms and/or operations described herein when the instructions are executed.

In one embodiment, the data storage circuitry 120, 220 and/or the memory circuitry 144 may further include or be in communication with volatile media (also referred to as volatile storage, memory, memory storage, memory circuitry and/or similar terms used herein interchangeably). In one embodiment, the volatile storage or memory may also include, such as but not limited to, RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the data storage circuitry 120, 220 and/or the memory circuitry 144 may be used to store at least portions of the databases, database instances, database management system entities, data, applications, programs, program modules, scripts, source code, object code, byte code, compiled code, interpreted code, machine code, executable instructions, and/or the like being executed by, for example, the processing circuitry 112, 132, 212. Thus, the databases, database instances, database management system entities, data, applications, programs, program modules, scripts, source code, object code, byte code, compiled code, interpreted code, machine code, executable instructions, and/or the like may be used to control certain aspects of the operation of the device 100, 200 with the assistance of the processing circuitry 112, 132, 212 and operating system.

In one embodiment, the data storage circuitry 120, 220 and/or the memory circuitry 144 may further include or be in communication with non-volatile media (also referred to as non-volatile storage, memory, memory storage, memory circuitry and/or similar terms used herein interchangeably). In one embodiment, the data storage circuitry 120, 220 and/or the memory circuitry 144 may include, such as, but not limited to, hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the data storage circuitry 120, 220 and/or the memory circuitry 144 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to may refer to a structured or unstructured collection of information/data that is stored in a computer-readable storage medium.

In various embodiments of the present disclosure, the data storage circuitry 120, 220 and/or the memory circuitry 144 may also be embodied as a data storage device or devices, as a separate database server or servers, or as a combination of data storage devices and separate database servers. Further, in some embodiments, data storage circuitry 120, 220 and/or the memory circuitry 144 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery system may be stored. Further, the information/data required for the operation of the recovery system may also be partially stored in the cloud data storage system and partially stored in a locally maintained data storage system. More specifically, data storage circuitry 120, 220 and/or the memory circuitry 144 may encompass one or more data stores configured to store information/data usable in certain embodiments.

The communications circuitry 116, 140, 216 may be any means such as a device or circuitry embodied in either hardware or a combination of hardware and software that is configured to receive and/or transmit data from/to a network and/or any other device, circuitry, or module in communication with the device 100, 200. In this regard, the communications circuitry 116, 140, 216 may include, for example, a network interface for enabling communications with a wired or wireless communication network and/or in accordance with a variety of networking protocols described herein. For example, the communications circuitry 116, 140, 216 may include one or more network interface cards, antennae, buses, switches, routers, modems, and supporting hardware and/or software, or any other device suitable for enabling communications via a network. Additionally, or alternatively, the communication interface may include the circuitry for interacting with the antenna(s) to cause transmission of signals via the antenna(s) or to handle receipt of signals received via the antenna(s).

In some embodiments, the device 100, 200 may include the display 114, 214 that may, in turn, be in communication with the processing circuitry 112, 132, 212 to display one or more of the created images to a user. In various examples of the present disclosure, the display 114, 214 may include a liquid crystal display (LCD), a light-emitting diode (LED) display, a plasma display panel (PDP), a quantum dot LED (QLED) display, or the like.

In some embodiments, the device 100, 200 may include the input/output circuitry 118, 142, 218, 242 that may, in turn, be in communication with the processing circuitry 112, 132, 212 to provide output to the user and, in some embodiments, to receive an indication of a user input. The input/output circuitry 118, 142, 218, 242 may comprise an interface, a mobile application, a kiosk, and/or the like. In some embodiments, the input/output circuitry 118, 142, 218, 242 may also include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., the data storage circuitry 120, 220 and/or the memory circuitry 144 and/or the like).

It is also noted that all or some of the information discussed herein can be based on data that is received, generated and/or maintained by one or more components of device 100, 200. In some embodiments, one or more external systems (such as a remote cloud computing and/or data storage system) may also be leveraged to provide at least some of the functionality discussed herein.

Figure 3:
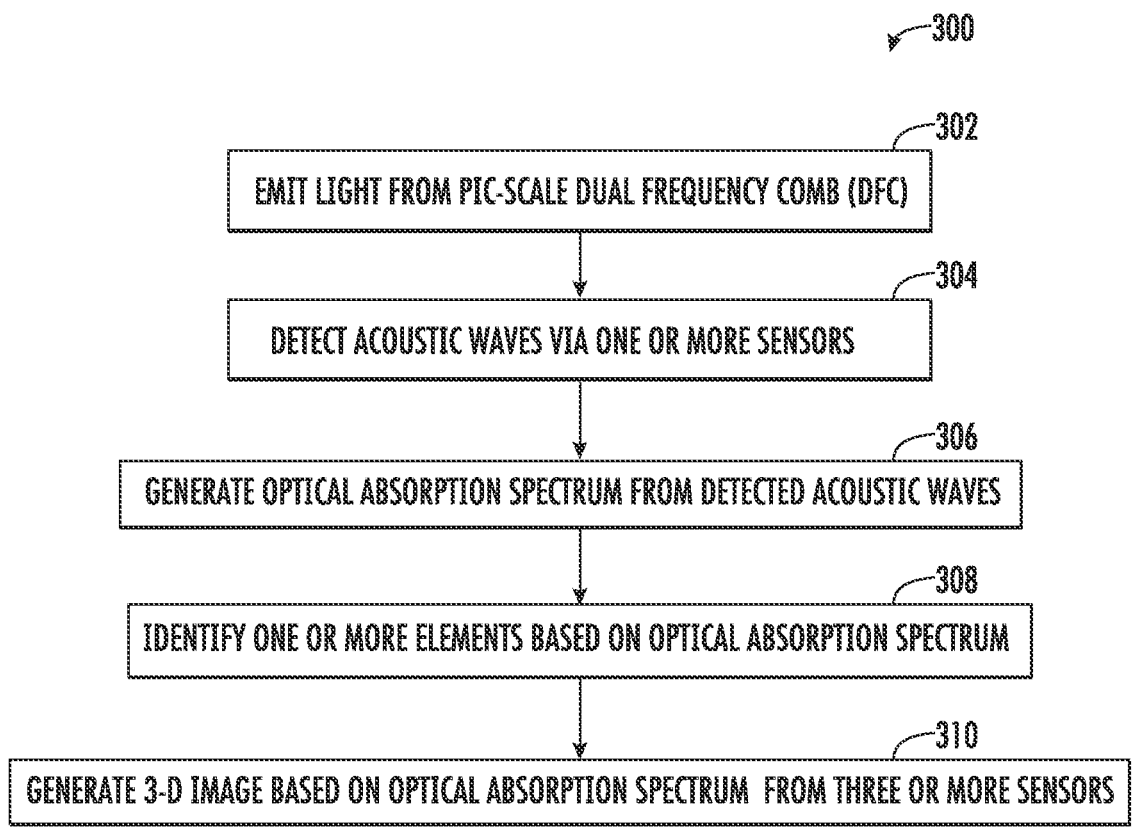
FIG. 3 is an example flowchart illustrating an example method of non-invasive medical imaging.

Reference will now be made to FIG. 3, which provide a flowchart illustrating example steps, processes, procedures, and/or operations in accordance with various embodiments of the present disclosure.

Various methods described herein, including, for example, example method as shown in FIG. 3, may provide various technical benefits and improvements. It is noted that each block of the flowchart, and combinations of blocks in the flowchart, may be implemented by various means such as hardware, firmware, circuitry and/or other devices associated with execution of software including one or more computer program instructions. For example, one or more of the procedures described in FIG. 3 may be embodied by computer program instructions, which may be stored by a non-transitory memory of an apparatus employing an embodiment of the present disclosure and executed by a processor in the apparatus. These computer program instructions may direct a computer or other programmable apparatus to function in a particular manner, such that the instructions stored in the computer-readable storage memory produce an article of manufacture, the execution of which implements the function specified in the flowchart block(s).

As described above and as will be appreciated based on this disclosure, embodiments of the present disclosure may be configured as methods, devices, and/or the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Similarly, embodiments may take the form of a computer program code stored on at least one non-transitory computer-readable storage medium. Any suitable computer-readable storage medium may be utilized including non-transitory hard disks, CD-ROMs, flash memory, optical storage devices, or magnetic storage devices.

Referring now to FIG. 3, an example method 300 is illustrated. In some embodiments, the example method 300 scans a bodily structure using a PIC-scale DFC to identify one or more elements within the bodily structure and generate a 3-D image.

The example method 300 starts at step/operation 302. At step/operation 302, a processor (such as, but not limited to, the processing circuitry 132 of the scanning portion 130 of the device 100 described above in connection with FIG. 1)

causes a DFC (such as, but not limited to, the DFC 134 of the scanning portion 130 of the device 100 described above in connection with FIG. 1) to emit multi-spectral light. The wavelengths or range of the multi-spectral light may be tuned to target one or more specific elements to be detected and identified, depending on the type of scan to be performed (e.g., ophthalmological).

Figure 4:
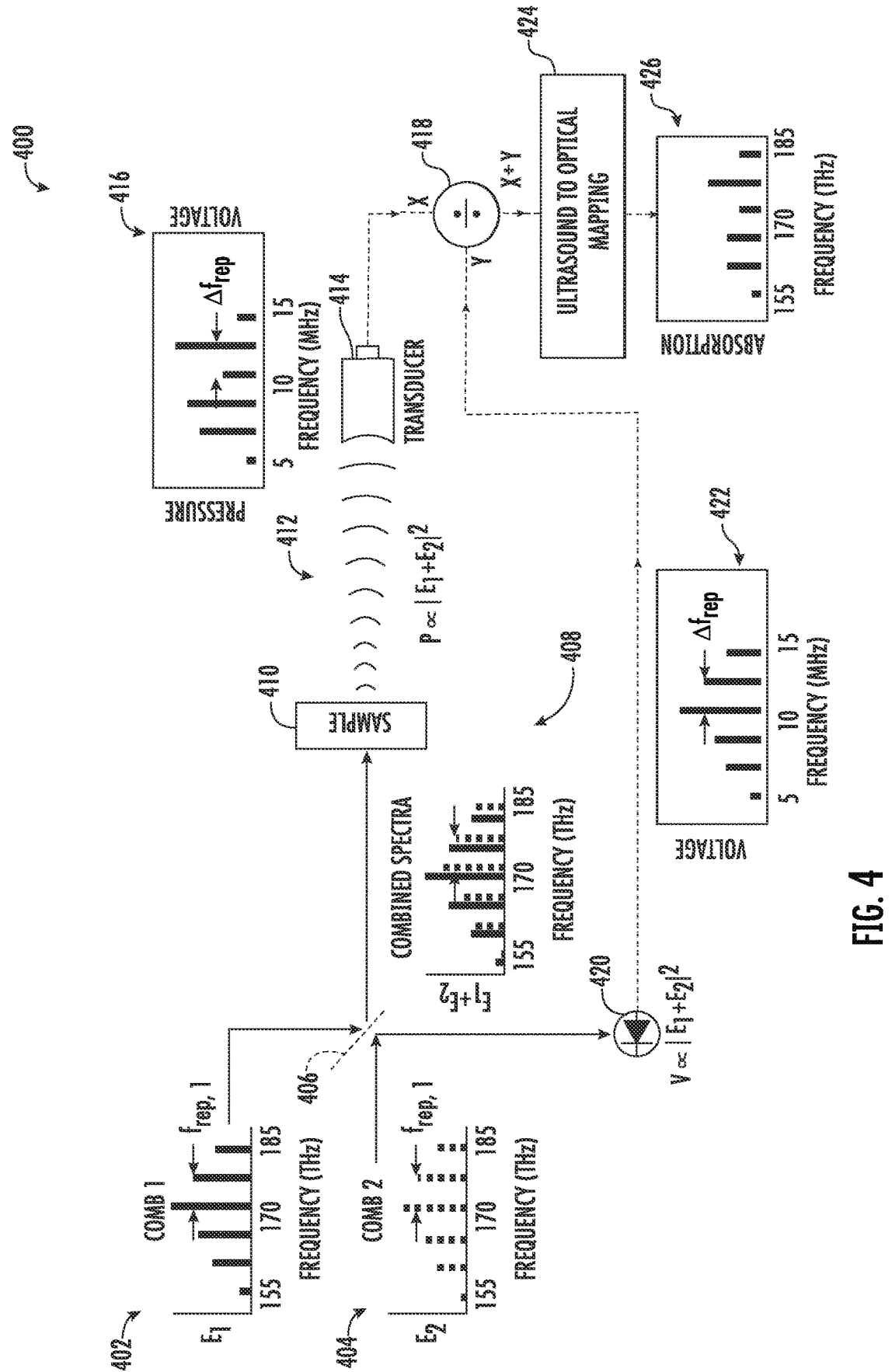
FIG. 4 illustrates example input and output spectra of an example device for non-invasive medical imaging in accordance with example embodiments of the present disclosure.

As is illustrated in FIG. 4 which illustrates the various input and output spectra 400 of various embodiments of the disclosure, the DFC produces two stabilized combs (e.g., Comb 1 spectra 402 and Comb 2 spectra 404) with slightly different repetition rates that are combined, such as by a mirror 406, to produce a combined spectra 408 that is directed at a bodily structure (e.g., sample 410 in FIG. 4) to be imaged. In various embodiments, any suitable range or ranges of frequencies may be emitted. In the illustrated example of FIG. 4, the emitted light is in the terahertz (THz) range, with an energy level of $E_1$ from Comb 1 and $E_2$ from Comb 2.

Figure 5:
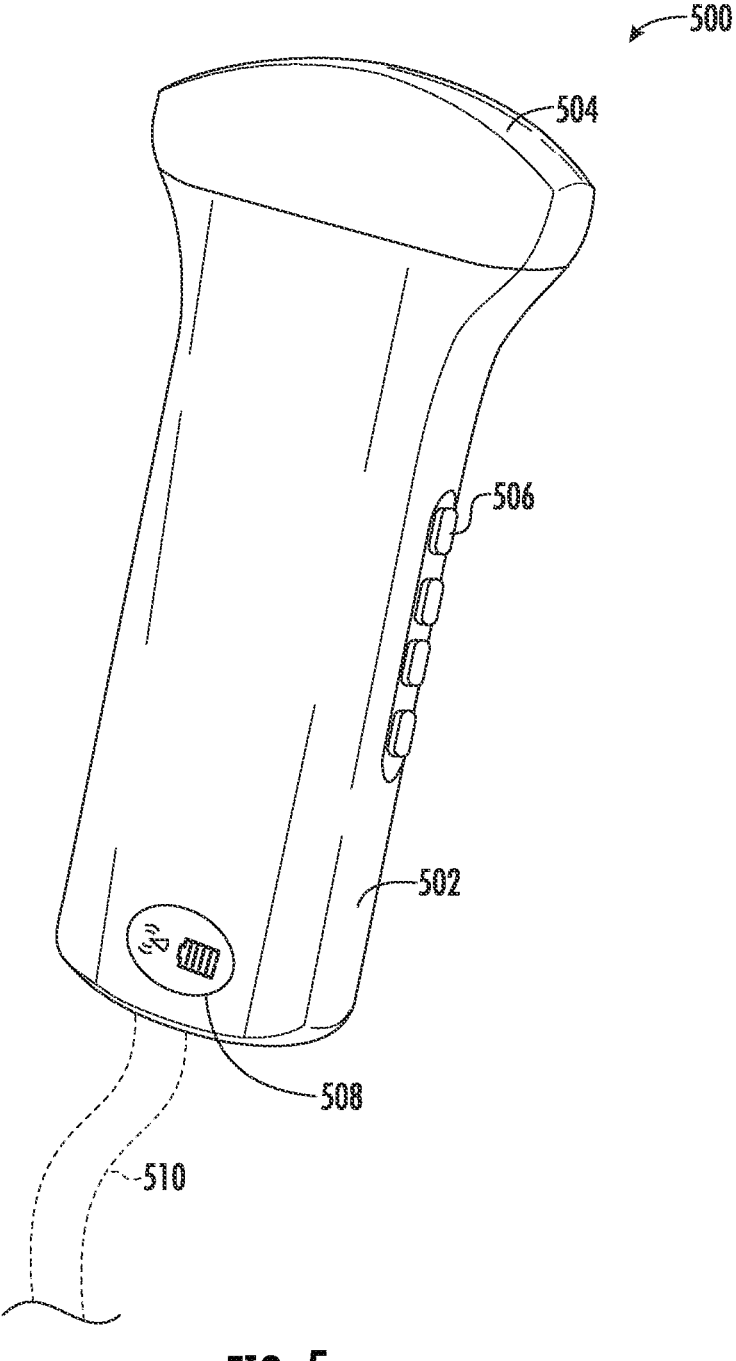
FIG. 5 illustrates an example hand-held wand of an example device for non-invasive medical imaging in accordance with example embodiments of the present disclosure.

In some embodiments, the multi-spectral light is emitted via a hand-held device such as is described below in relation to FIG. 5. In some embodiments, the multi-spectral light is emitted via a body-worn device such as is described below in relation to FIG. 6.

Returning now to FIG. 3, at step/operation 304, one or more sensors (such as, but not limited to, the transducer(s) 138 of the scanning portion 130 of the device 100 described above in connection with FIG. 1) detect acoustic waves from thermo-elastic changes in one or more elements within the one or more bodily structures exposed to the light emitted at step/operation 304.

As is illustrated in FIG. 4, the acoustic waves 412, which have a pressure "p" that is proportional to the square of the sum of $E_1$ from Comb 1 and $E_2$ from Comb 2 and a frequency in the megahertz (MHz) range (an example spectra 416 is illustrated), are detected by a transducer 414. In various embodiments, multiple transducers (typically at least three) detect the acoustic waves from each emission point to enable creation of a 3-D image.

Returning now to FIG. 3, at step/operation 306, a processor (such as, but not limited to, the processing circuitry 132 of the scanning portion 130 of the device 100 described above in connection with FIG. 1) generates an optical absorption spectrum from the acoustic waves detected at step/operation 304. This step is often referred to as demodulation. Any suitable demodulation technique may be used.

As is illustrated in FIG. 4, one example method to get optical absorption information from the modulated acoustic waves is to first normalize the transducer's signal to a reference radio frequency (RF) spectrum generated on a photodiode (such as photodiode 420 in FIG. 4) from the dual comb light. The output voltage from the photodiode is proportional to the square of the sum of $E_1$ from Comb 1 and $E_2$ from Comb 2 and has a frequency in the MHz range (an example spectra 422 is illustrated). In this example method illustrated in FIG. 4, the RF spectrum derived from the voltage signal from the transducer is divided (such as by divider 418) by the RF spectrum derived from the voltage from the reference photodiode. Once normalized, the RF spectrum can be directly mapped back to the optical (where the sample diagnostics reside) by simple properties of the dual combs (indicated by block 424), resulting in the optical absorption spectra (such as spectra 426 of FIG. 4) of the imaged bodily structure.

Returning now to FIG. 3, at step/operation 308, a processor (such as, but not limited to, the processing circuitry 132 of the scanning portion 130 of the device 100 described above in connection with FIG. 1) identifies one or more elements based on the optical absorption spectrum generated at step/operation 306. As described above, various embodiments of the disclosure use the generated optical absorption spectrum to identify one or more elements (e.g., cells, molecules, etc.) based on a predetermination of which types of cells, molecules, tissues, structures, etc., absorb light at which frequency.

In the example shown in FIG. 3, at step/operation 310, a processor (such as, but not limited to, the processing circuitry 112 of the base unit 110 of the device 100 described above in connection with FIG. 1) generates a 3-D image based on the optical absorption spectrum generated at step/operation 306. In various embodiments of the disclosure, the optical absorption spectra generated from at least three different transducers are used to generate a 3-D image, using a processing methodology similar to that of conventional photoacoustic ultrasound imaging.

In some embodiments, the method 300 repeats steps/operations 302-310 every time a user actuates the device to scan.

As described above, a medical imaging device of embodiments of the invention may comprise a hand-held scanning portion and/or a body-worn scanning portion. Such a hand-held scanning portion may be easily grasped by a user and moved into various positions relative to a patient's body for scanning. Referring now to FIG. 5, a hand-held scanning wand 500 comprises a main body 502, a scanning head 504, one or more user input elements 506 (e.g., buttons, knobs, etc.), one or more user output elements 508 (e.g., indicator lights), and optionally a cable 510 connecting the hand-held scanning wand 500 to a base unit (not illustrated). In various embodiments, at least one emission point and typically at least three transducers are positioned in the scanning head 504 facing outward from the curved face of the scanning head 504. In various embodiments, the hand-held scanning wand 500 is about the size of a smartphone, enabling the hand-held scanning wand 500 to be easily grasped and moved by a user.

As described above, in some embodiments the DFC resides in the scanning portion (as illustrated in FIG. 1), while in some other the DFC resides in the base unit (as illustrated in FIG. 2). For embodiments in which the DFC resides in the scanning portion, the hand-held scanning wand 500 would house the DFC and may further house processing circuitry, communications circuitry, input/output circuitry, and/or memory circuitry. In such embodiments, a wireless connection may be used between the base unit and the hand-held scanning wand since light does not need to be transmitted between the base unit and the hand-held scanning wand.

For other embodiments in which the DFC resides in the base unit, a physical connection (e.g., an optical fiber cable) is needed between the base unit and the hand-held scanning wand for transmission of light between the DFC in the base unit and the scanning portion. In addition to the optical fiber cable, such embodiments may also have a metallic communications cable between the base unit and the hand-held scanning wand for transmission of control signals, etc.

Figure 6:
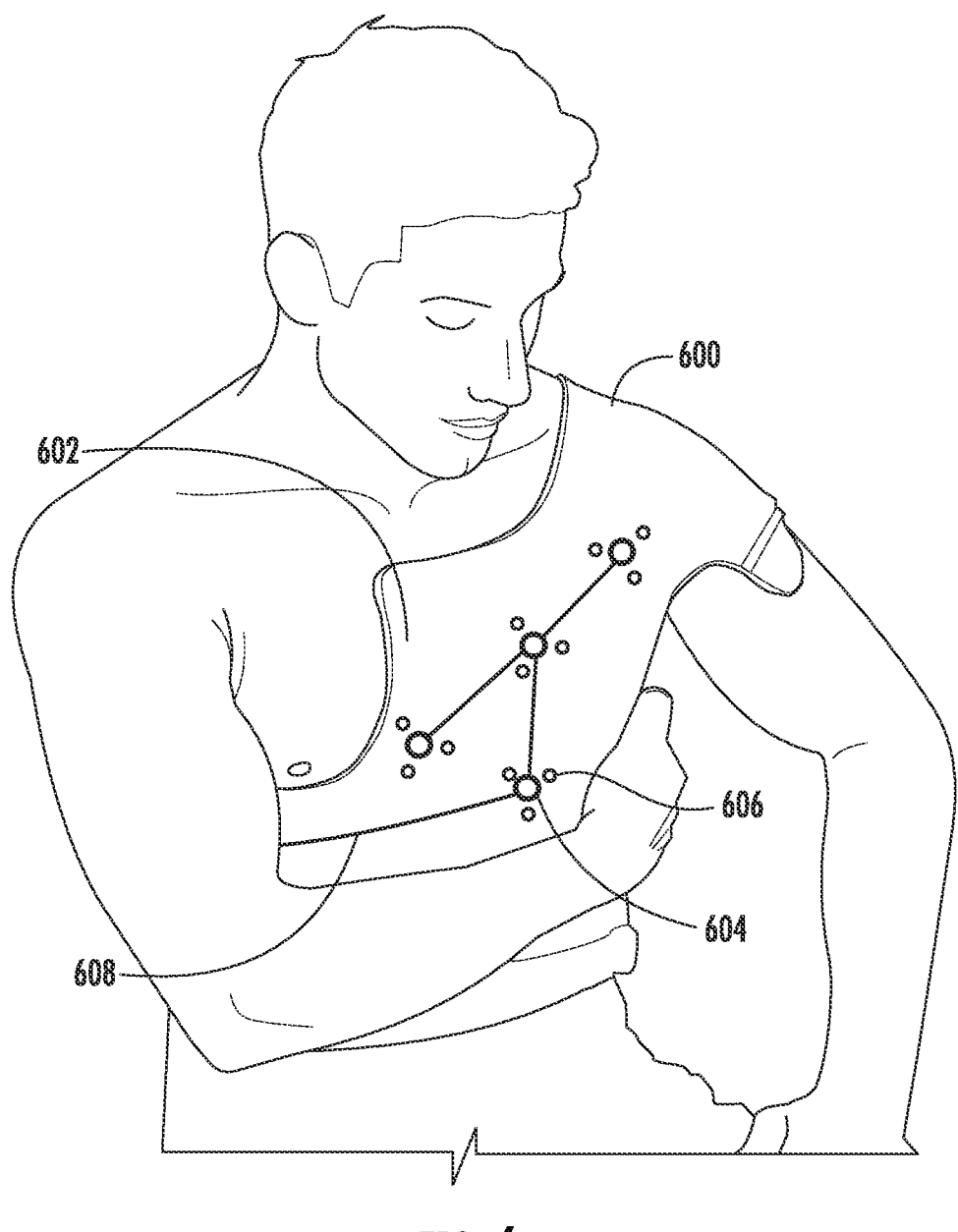
FIG. 6 illustrates an example body-worn portion of an example device for non-invasive medical imaging in accordance with example embodiments of the present disclosure.

A body-worn scanning portion may cover or encircle some part or parts of a patient's body, such as the trunk, the abdomen, an arm, or a leg. Such a body-worn scanning portion may be secured to the patient's body, such as via one or more straps or the like. Such a body-worn scanning portion may be in the form of a vest, harness, sleeve, or any other suitable form. Referring now to FIG. 6, a body-worn vest 600 for scanning a patient's heart and surrounding structures (e.g., aortic arch) is illustrated that comprises a main vest portion 602 that covers the patient's left chest, left axillary region, and left upper back (not illustrated) to generate images from a plurality of different angles/views. The body-worn vest 600 comprises a plurality of light emission points 604, each connected via optical fiber cables 608 to a DFC (which may be located on the body-worn vest 600 or separate from the body-worn vest 600 (for example, in a base unit). Although only four emission points 604 are illustrated, such a body-worn vest may comprise any suitable number of emission points at many different locations on the body-worn vest. Adjacent to each emission point, there are typically at least three sensors 606 (e.g., transducers) to receive the acoustic waves generated as a result of the light emitted by the respective emission point (any suitable number of sensors may be provided).

For a chest-worn device, it is typically desirable that at least one emission point align with an intercostal space to enable sufficient light penetration into the patient's chest. Because of different body shapes, sizes, etc., it is desirable to have a sufficient number of emission points at various positions to ensure that at least one is aligned with an intercostal space. In various embodiments, a test scan is conducted with each emission point to determine the strength of the acoustic waves generated in response to the emission from each emission point. Based on the determined strength of the test acoustic waves generated, it can be determined which emission point(s) is/are aligned with an intercostal space such that only that emission point(s) is used for scanning.

Operations and processes described herein support combinations of means for performing the specified functions and combinations of operations for performing the specified functions. It will be understood that one or more operations, and combinations of operations, may be implemented by special purpose hardware-based computer systems which perform the specified functions, or combinations of special purpose hardware and computer instructions.

In some example embodiments, certain ones of the operations herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

The foregoing method and process descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," and similar words are not intended to limit the order of the steps; these words are simply used to guide the reader through the description of the methods. Further, any reference to claim elements in the singular, for example, using the articles "a," "an" or "the," is not to be construed as limiting the element to the singular and may, in some instances, be construed in the plural.

While various embodiments in accordance with the principles disclosed herein have been shown and described above, modifications thereof may be made by one skilled in the art without departing from the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present disclosure. Furthermore, any advantages and features described above may relate to specific embodiments but shall not limit the application of such issued claims to processes and structures accomplishing any or all of the above advantages or having any or all of the above features.

In addition, the section headings used herein are provided for consistency with the suggestions under 37 C.F.R. § 1.77 or to otherwise provide organizational cues. These headings shall not limit or characterize the disclosure set out in any claims that may issue from this disclosure. For instance, a description of a technology in the "Background" is not to be construed as an admission that certain technology is prior art to any disclosure in this disclosure. Neither is the "Summary" to be considered as a limiting characterization of the disclosure set forth in issued claims. Furthermore, any reference in this disclosure to "disclosure" or "embodiment" in the singular should not be used to argue that there is only a single point of novelty in this disclosure. Multiple embodiments of the present disclosure may be set forth according to the limitations of the multiple claims issuing from this disclosure, and such claims accordingly define the disclosure, and their equivalents, which are protected thereby. In all instances, the scope of the claims shall be considered on their own merits in light of this disclosure but should not be constrained by the headings set forth herein.

Also, systems, subsystems, apparatuses, techniques, and methods described and illustrated in the various embodiments as discrete or separate may be combined or integrated with other systems, modules, techniques, or methods without departing from the scope of the present disclosure. Other devices or components shown or discussed as coupled to, or in communication with, each other may be indirectly coupled through some intermediate device or component, whether electrically, mechanically, or otherwise. Other examples of changes, substitutions, and alterations are ascertainable by one skilled in the art and could be made without departing from the scope disclosed herein.

Many modifications and other embodiments of the disclosure set forth herein will come to mind to one skilled in the art to which these embodiments pertain having the benefit of teachings presented in the foregoing descriptions and the associated figures. Although the figures only show certain components of the apparatuses and systems described herein, various other components may be used in conjunction with the components and structures disclosed herein. Therefore, it is to be understood that the disclosure is not to be limited to the specific embodiments disclosed and that modifications and other embodiments are intended to be included within the scope of the appended claims. For example, the various elements or components may be combined, rearranged, or integrated in another system or certain features may be omitted or not implemented. Moreover, the steps in any method described above may not necessarily occur in the order depicted in the accompanying drawings, and in some cases one or more of the steps depicted may occur substantially simultaneously, or additional steps may be involved. Although specific terms are employed herein, they are used in a generic and descriptive sense only and not for purposes of limitation.

What is claimed is:

1. A device for non-invasive medical imaging, the device comprising:
   a photonic integrated circuit (PIC)-scale dual frequency comb (DFC);
   a hand-held wand comprising (i) a plurality of emission points for emitting light simultaneously from first emission point at a first frequency and a second emission point at a second frequency from the PIC-scale DFC and (ii) a plurality of groups of at least three sensors, wherein a first group of the at least three sensors is placed corresponding to the first emission point and a second group of the at least three sensors placed corresponding to the second emission point, wherein each of the groups of the at least three sensors is physically distinct and spatially isolated from other sensor groups, and wherein the first group of the at least three sensors is configured to detect acoustic waves generated in response to the emitted light at the first frequency, wherein the second group of the at least three sensors is configured to detect acoustic waves generated in response to the emitted light at the second frequency, wherein the hand-held wand is adapted to direct the emitted light at one or more bodily structures, wherein each of the groups of the at least three sensors are adapted to detect acoustic waves from thermo-elastic changes in at least one of one or more elements within the one or more bodily structures exposed to the emitted light from a corresponding one of the plurality of emission points; and
   at least one processing element for (i) generating an optical absorption spectrum based on the detected acoustic waves from each of the groups of at least three sensors, (ii) identifying at least one of the one or more elements within the one or more bodily structures exposed to the emitted light based on the optical absorption spectrum, and (iii) generating a three-dimensional (3-D) image of the one or more elements based on the optical absorption spectrum from the detected acoustic waves from each of the groups of at least three sensors.

2. The device of claim 1, wherein the PIC-scale DFC resides in the wand.

3. The device of claim 1, further comprising a base unit separate from the wand and a display element within the base unit for displaying the generated 3-D image.

4. The device of claim 3, wherein the PIC-scale DFC resides in the base unit.

5. The device of claim 4, further comprising one or more optical fiber cables for carrying light from the PIC-scale DFC in the base unit to the plurality of emission points in the wand.

6. The device of claim 3, wherein the at least one processing element resides in the wand or the base unit.

7. The device of claim 3, wherein communication between the wand and the base unit is wired or wireless.

8. The device of claim 1, wherein the at least three sensors of each group comprise at least three transducers.

9. The device of claim 1, wherein the at least one processing element provides the generated 3-D image to an artificial intelligence algorithm.

10. The device of claim 1, wherein the one or more elements comprise two elements;

wherein the two elements comprise oxygenated blood and non-oxygenated blood; and
wherein generating the 3-D image by the at least one processing element comprises generating a 3-D image of one or more blood vessels based on the detected acoustic waves from the oxygenated blood and the non-oxygenated blood.

11. The device of claim 10, wherein the one or more bodily structures comprises an eyeball; and
wherein relatively shorter wavelengths of light are used to image a posterior portion of the eyeball and relatively longer wavelengths of light are used to image an anterior portion of the eyeball.

12. The device of claim 1, wherein the one or more bodily structures comprises skin.

13. A method for non-invasive medical imaging, the method comprising:
   emitting light simultaneously from a first emission point at a first frequency and a second emission point at a second frequency from a photonic integrated circuit (PIC)-scale dual frequency comb (DFC) via a hand-held device directed at one or more bodily structures;
   detecting acoustic waves from thermo-elastic changes in at least one or more elements within the one or more bodily structures exposed to the emitted light from the first emission point and the second emission point via a plurality of groups of at least three sensors in the hand-held device, wherein a first group of the at least three sensors is placed corresponding to the first emission point and a second group of the at least three sensors is placed corresponding to the second emission point, wherein each of the groups of the at least three sensors is physically distinct and spatially isolated from other sensor groups, wherein the first group of the at least three sensors is configured to detect acoustic waves generated in response to the emitted light at the first frequency, and wherein the second group of the at least three sensors is configured to detect acoustic waves generated in response to the emitted light at the second frequency;
   generating an optical absorption spectrum from the detected acoustic waves; and
   identifying at least one of the one or more elements within the one or more bodily structures exposed to the emitted light based on the optical absorption spectrum.

14. The method of claim 13, wherein the at least three sensors of each group comprise one or more transducers.

15. The method of claim 13, wherein the method further comprises:
   generating an optical absorption spectrum from the detected acoustic waves from each group of at least three sensors; and
   generating a three-dimensional (3-D) image of the one or more elements based on the optical absorption spectrum from the detected acoustic waves from each of the three or more sensors.

16. The method of claim 15, further comprising displaying the generated 3-D image.

17. The method of claim 15, further comprising providing the generated 3-D image to an artificial intelligence algorithm.

18. The method of claim 15, wherein the one or more elements comprise two elements;
   wherein the two elements comprise oxygenated blood and non-oxygenated blood; and wherein generating the 3-D image comprises generating a 3-D image of one or more blood vessels based on the detected acoustic waves from the oxygenated blood and the non-oxygenated blood.

19. The method of claim 18, wherein the one or more bodily structures comprises an eyeball; and wherein relatively shorter wavelengths of light are used to image a posterior portion of the eyeball and relatively longer wavelengths of light are used to image an anterior portion of the eyeball.

20. The method of claim 13, wherein the one or more bodily structures comprises skin.

\* \* \* \* \*